(12) United States Patent
Brockway et al.

(10) Patent No.: US 7,953,484 B2
(45) Date of Patent: *May 31, 2011

(54) METHOD AND APPARATUS FOR OPTIMIZATION OF CARDIAC RESYNCHRONIZATION THERAPY USING HEART SOUNDS

(75) Inventors: Marina Brockway, Shoreview, MN (US); William C. Lincoln, Richmond, VA (US); Gerrard M. Carlson, Champlin, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 350 days.

This patent is subject to a terminal disclaimer.

(21) Appl. No.: 11/687,812

(22) Filed: Mar. 19, 2007

(65) Prior Publication Data
US 2007/0162080 A1 Jul. 12, 2007

Related U.S. Application Data

(63) Continuation of application No. 10/865,498, filed on Jun. 10, 2004, now Pat. No. 7,209,786.

(51) Int. Cl.
*A61N 1/00* (2006.01)
(52) U.S. Cl. .............................. 607/17; 607/9
(58) Field of Classification Search .................. 607/1, 2, 607/9, 17–18; 600/508, 509, 513, 528
See application file for complete search history.

(56) References Cited

U.S. PATENT DOCUMENTS

| 4,586,514 | A | 5/1986 | Schlager et al. |
| 4,981,139 | A | 1/1991 | Pfohl |
| 5,010,889 | A | 4/1991 | Bredesen et al. |
| 5,012,815 | A | 5/1991 | Bennett, Jr. et al. |
| 5,179,947 | A | 1/1993 | Meyerson et al. |
| 5,544,661 | A | 8/1996 | Davis et al. |
| 5,554,177 | A * | 9/1996 | Kieval et al. .................... 607/17 |
| 5,674,256 | A | 10/1997 | Carlson |
| 5,700,283 | A | 12/1997 | Salo |
| 5,792,195 | A | 8/1998 | Carlson et al. |
| 5,836,987 | A | 11/1998 | Baumann et al. |
| 5,935,081 | A | 8/1999 | Kadhiresan |
| 6,026,324 | A | 2/2000 | Carlson |

(Continued)

FOREIGN PATENT DOCUMENTS

WO WO-0156651 A1 8/2001

(Continued)

OTHER PUBLICATIONS

"International Search Report and Written Opinion for Application No. PCT/US2005/019773, mailed Nov. 24, 2005", 16 pgs.

(Continued)

*Primary Examiner* — Mark W Bockelman
*Assistant Examiner* — Elizabeth K So
(74) *Attorney, Agent, or Firm* — Schwegman, Lundberg & Woessner, P.A.

(57) ABSTRACT

A cardiac rhythm management system provides for assessment of cardiac mechanical dyssynchrony based on heart sound morphology and optimization of pacing parameters based on the effect of pacing on the cardiac mechanical dyssynchrony assessment. A degree of cardiac mechanical dyssynchrony is measured by the time delay between tricuspid valve closure and mitral valve closure and/or the time delay between pulmonary valve closure and aortic valve closure. A cardiac resynchronization therapy is optimized by determining therapy parameters to provide an approximately minimum degree of cardiac mechanical dyssynchrony by cardiac pacing.

20 Claims, 7 Drawing Sheets

U.S. PATENT DOCUMENTS

| | | | |
|---|---|---|---|
| 6,044,298 | A | 3/2000 | Salo et al. |
| 6,044,299 | A | 3/2000 | Nilsson |
| 6,058,329 | A | 5/2000 | Salo et al. |
| 6,144,880 | A | 11/2000 | Ding et al. |
| 6,193,668 | B1 | 2/2001 | Chassaing et al. |
| 6,272,377 | B1 | 8/2001 | Sweeney et al. |
| 6,351,673 | B1 | 2/2002 | Ding et al. |
| 6,360,127 | B1 | 3/2002 | Ding et al. |
| 6,366,811 | B1 | 4/2002 | Carlson |
| 6,409,675 | B1 | 6/2002 | Turcott |
| 6,477,406 | B1 | 11/2002 | Turcott |
| 6,478,746 | B2 | 11/2002 | Chassaing et al. |
| 6,480,733 | B1 | 11/2002 | Turcott |
| 6,491,639 | B1 | 12/2002 | Turcott |
| 6,520,924 | B2 | 2/2003 | Lee |
| 6,527,729 | B1 | 3/2003 | Turcott |
| 6,542,775 | B2 | 4/2003 | Ding et al. |
| 6,626,842 | B2 | 9/2003 | Oka |
| 6,643,548 | B1 | 11/2003 | Mai et al. |
| 6,650,940 | B1 | 11/2003 | Zhu et al. |
| 6,665,564 | B2 | 12/2003 | Lincoln et al. |
| 6,684,103 | B2 | 1/2004 | Ding et al. |
| 6,792,308 | B2 | 9/2004 | Corbucci |
| 6,810,287 | B2 | 10/2004 | Zhu et al. |
| 6,885,889 | B2 | 4/2005 | Chinchoy |
| 6,963,777 | B2 | 11/2005 | Lincoln et al. |
| 7,079,895 | B2 | 7/2006 | Verbeek et al. |
| 7,079,896 | B1 * | 7/2006 | Park et al. ........................ 607/17 |
| 7,113,825 | B2 * | 9/2006 | Pastore et al. .................... 607/14 |
| 7,115,096 | B2 | 10/2006 | Siejko et al. |
| 7,123,962 | B2 | 10/2006 | Siejko et al. |
| 7,139,609 | B1 * | 11/2006 | Min et al. ........................ 607/17 |
| 7,206,636 | B1 * | 4/2007 | Turcott ............................ 607/17 |
| 7,209,786 | B2 * | 4/2007 | Brockway et al. ............... 607/17 |
| 2002/0072684 | A1 | 6/2002 | Stearns |
| 2002/0151938 | A1 | 10/2002 | Corbucci |
| 2003/0055461 | A1 | 3/2003 | Girouard et al. |
| 2003/0105496 | A1 | 6/2003 | Yu et al. |
| 2003/0144702 | A1 | 7/2003 | Yu et al. |
| 2003/0144703 | A1 | 7/2003 | Yu et al. |
| 2003/0153952 | A1 | 8/2003 | Auricchio et al. |
| 2003/0171791 | A1 | 9/2003 | KenKnight et al. |
| 2003/0208240 | A1 | 11/2003 | Pastore et al. |
| 2004/0073093 | A1 | 4/2004 | Hatlestad |
| 2004/0106960 | A1 | 6/2004 | Siejko et al. |
| 2004/0106961 | A1 | 6/2004 | Siejko et al. |
| 2004/0122484 | A1 | 6/2004 | Hatlestad et al. |
| 2004/0127792 | A1 | 7/2004 | Siejko et al. |
| 2005/0090870 | A1 | 4/2005 | Hine et al. |
| 2005/0102002 | A1 | 5/2005 | Salo et al. |
| 2005/0148896 | A1 | 7/2005 | Siejko et al. |
| 2005/0149136 | A1 | 7/2005 | Siejko et al. |
| 2005/0203579 | A1 | 9/2005 | Sowelam et al. |
| 2005/0256542 | A1 | 11/2005 | Pastore et al. |
| 2006/0030892 | A1 | 2/2006 | Kadhiresan et al. |
| 2006/0282000 | A1 | 12/2006 | Zhang et al. |

FOREIGN PATENT DOCUMENTS

| | | | |
|---|---|---|---|
| WO | WO-2004/060483 | A1 | 7/2004 |
| WO | WO-2005122902 | A1 | 12/2005 |

OTHER PUBLICATIONS

Brockway, Marina , et al., "Method and Apparatus for Monitoring Heart Failure Patients With Cardiopulmonary Comorbidities", U.S. Appl. No. 10/897,856, filed Jul. 23, 2004, 54 pages.

Bulgrin, J. R., et al., "Comparison of Short-Time Fourier, Wavelet ant Time-Domain Analyses of Intracardiac Sounds", *Biomedical Sciences Instrumentation*, 29, (1993),465-472.

Kinderman, Michael , et al., "Optimizing the AV Delay in DDD Pacemaker Patients with High Degree AV Block: Mitral Valve Doppler Versus Impedance Cardiography", *PACE*, vol. 20, pp. 2453-2462, (Oct. 1997),2453-2462.

Leatham, A., "Splitting of the First and Second Heart Sounds", *Lancet*, 267 (6839), (Sep. 25, 1954),607-614.

Leonelli, Fabio M., et al., "Systolic and Diastolic Effects of Variable Atroventricular Delay and Patients with Complete Hear Block and Normal Ventricular Function", *Amer. J-Cardiology*, vol. 80, pp. 294-298, (Aug. 1, 1997),294-298.

Maile, Keith R., et al., "A Dual-Use Sensor for Rate Responsive Pacing and Heart Sound Monitoring", U.S. Appl. No. 10/703,175, filed Nov. 6, 2003, 41 pgs.

Maile, Keith R., et al., "Determining A Patient's Posture From Mechanical Vibrations Of The Heart", U.S. Appl. No. 10/900,570, filed Jul. 28, 2004, 24 pgs.

Obaidat, M. S., et al., "Performance of the Short-Time Fourier Transform and Wavelet Transform to Phonocardiogram Signal Analysis", *Proceedings of the 1992 ACM/SIGAPP Symposium on Applied Computing ACM*, Applied Computing: Technological Challenges of the 1990s,(1992),856-862.

Pastore, Joseph M., et al., "Method and Apparatus for Detecting Oscillations in Cardiac Rhythm with Electrogram Signals", U.S. Appl. No. 11/184,325, filed Jul. 19, 2005, 22 Pages.

Ritter, P., et al., "New Method for Determining the Optimal Atrio-Ventricular Delay in Patients Place in DDD Mode for Complete Atrio-Ventricular Block", NASPE abstract #237, p. 885, (1995),3.

Siejko, K. Z., et al., "Method for Correction of Posture Dependence on Heart Sounds", U.S. Appl. No. 11/037,275, filed Jan. 18, 2005, 26 pgs.

Wariar, R. , et al., "Systems and Methods for Multi-Axis Cardiac Vibration Measurements", U.S. Appl. No. 11/135,985, filed May 24, 2004.

Wood, J. C., et al., "Time-Frequency Transforms: A New Approach to First Heart Sound Frequency Dynamics", *IEEE Transactions on Biomedical Engineering*, 39 (7), IEEE Service Center, US,(Jul. 1, 1992),730-740.

Zhang, Y., et al., "Ischemia Detection Using A Heart Sound Sensor", U.S. Appl. No. 11/148,107, filed Jun. 8, 2005, 41 pgs.

Obaidat, M. S., et al., "Performance of the short-time Fourier transform and wavelet transform to phonocardiogram signal analysis", *Database Inspec [Online] The Institution Of Electrical Engineers, Stevenage, GB*, (1992) 1 pg.

* cited by examiner

METHOD AND APPARATUS FOR OPTIMIZATION OF CARDIAC RESYNCHRONIZATION THERAPY USING HEART SOUNDS

CROSS-REFERENCE TO RELATED APPLICATIONS

This application is a continuation of U.S. patent application Ser. No. 10/865,498 filed on Jun. 10, 2004, which is now issued as U.S. Pat. No. 7,209,786, the specification of which is incorporated herein by reference.

This application is related to co-pending, commonly assigned, U.S. patent application Ser. No. 10/334,694, entitled "METHOD AND APPARATUS FOR MONITORING OF DIASTOLIC HEMODYNAMICS," filed Dec. 30, 2002, and U.S. patent application Ser. No. 10/307,896, "PHONOCARDIOGRAPHIC IMAGE-BASED ATRIO-VENTRICULAR DELAY OPTIMIZATION," filed Dec. 2, 2002, now issued as U.S. Pat. No. 7,123,962, which are hereby incorporated by reference in their entirety.

FIELD OF THE INVENTION

This document generally relates to cardiac rhythm management (CRM) systems and particularly, but not by way of limitation, to such systems providing for optimization of cardiac therapy using heart sounds.

BACKGROUND

The heart is the center of a person's circulatory system. It includes a complex electromechanical system performing two major pumping functions. The heart includes four chambers: right atrium (RA), right ventricle (RV), left atrium (LA), and left ventricle (LV). The RA draws deoxygenated blood from organs of the body and injects it into the RV through the tricuspid valve. The RV pumps the deoxygenated blood to the lungs through the pulmonary valve. The blood gets oxygenated in the lungs. The LA draws oxygenated blood from the lungs and injects it into the LV through the mitral valve. The LV pumps the oxygenated blood to the organs of the body, through the aortic valve, to provide the organs with their metabolic needs for oxygen. These mechanical pumping functions are accomplished by contractions of the myocardium (heart muscles). In a normal heart, the sinoatrial (SA) node, the heart's natural pacemaker, generates electrical impulses, called action potentials, that propagate through an electrical conduction system to various regions of the heart to excite myocardial tissues in these regions. Coordinated delays in the propagations of the action potentials in a normal electrical conduction system cause the muscles in various regions of the heart to contract in mechanical synchrony such that the pumping functions are performed efficiently.

The normal pumping functions of the heart, indicated by the normal hemodynamic performance, require a normal electrical system to generate the action potentials and deliver them to designated portions of the myocardium with proper timing, a normal myocardium capable of contracting with sufficient strength, and a normal electromechanical association such that all regions of the heart are excitable by the action potentials. A blocked or otherwise abnormal electrical conduction and/or deteriorated myocardial tissue cause dyssynchronous contraction of the heart, resulting in poor hemodynamic performance, including a diminished blood supply to the heart and the rest of the body. The condition where the heart fails to pump enough blood to meet the body's metabolic needs is known as heart failure.

Because the pumping functions are mechanical functions, the hemodynamic performance is ultimately determined by the mechanical synchrony of the heart. For this and other reasons, there is a need for a direct assessment of cardiac mechanical dyssynchrony. The assessment serves as a direct measure of efficacy for a cardiac therapy restoring the cardiac mechanical synchrony.

SUMMARY

A cardiac rhythm management (CRM) system provides for assessment of cardiac mechanical dyssynchrony based on heart sound morphology and optimization of pacing parameters based on the effect of pacing on the cardiac mechanical dyssynchrony assessment. A degree of cardiac mechanical dyssynchrony is measured by the time delay between tricuspid valve closure and mitral valve closure and/or the time delay between pulmonary valve closure and aortic valve closure. A cardiac resynchronization therapy is optimized by determining therapy parameters to provide an approximately minimum degree of cardiac mechanical dyssynchrony by cardiac pacing.

In one embodiment, a system for analyzing a heart includes a heart sound input, a heart sound detector, and a computer-based heart sound morphology analyzer. The heart sound input receives one or more signals indicative of heart sounds. The heart sound detector detects heart sounds of at least one predetermined type. The computer-based heart sound morphology analyzer produces at least one dyssynchrony parameter indicative of a degree of cardiac mechanical dyssynchrony based on measurements of the detected heart sounds. The heart sound morphology analyzer includes a heart sound measurement module to measure one or more parameters each based on at least one morphological feature of the detected heart sounds. The morphological feature indicates a time interval between closures of a first cardiac valve and a second cardiac valve of the heart in one cardiac cycle.

In one embodiment, a system for analyzing a heart includes an implantable system and an external system communicating with the implantable system. The implantable system includes one or more implantable heart sound sensors and an implantable medical device. The one or more implantable heart sound sensors sense one or more heart sound signals each indicative of heart sounds. The implantable medical device includes an implant controller to process the one or more heart sound signals and an implant telemetry module to transmit the one or more heart sound signals to the external system. The external system includes an external telemetry module to receive the one or more heart sound signals and an external controller to process the one or more heart sound signals. The external controller includes a heart sound morphology analyzer to produce at least one dyssynchrony parameter indicative of a degree of cardiac mechanical dyssynchrony. The heart sound morphology analyzer includes a heart sound measurement module to measure one or more parameters each based on at least one morphological feature of heart sounds of at least one predetermined type. The morphological feature indicates a time interval between closures of a first cardiac valve and a second cardiac valve of a heart in one cardiac cycle.

In one embodiment, a method for operating a cardiac pacemaker is provided. One or more heart sound signals indicative of heart sounds are received. Heart sounds of at least one predetermined type are detected. One or more dyssynchrony parameters each indicative of a degree of cardiac mechanical dyssynchrony are produced based on at least one morphological feature of the detected heart sounds by executing an automated cardiac mechanical dyssynchrony algorithm. One or more pacing parameters for minimizing the degree of cardiac mechanical dyssynchrony are determined based on the one or more dyssynchrony parameters.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that fonn a part thereof, each of which are not to be taken in a limiting sense. The scope of the present invention is defined by the appended claims and their equivalents.

BRIEF DESCRIPTION OF THE DRAWINGS

In the drawings, which are for illustrative purposes only and not necessarily drawn to scale, like numerals describe similar components throughout the several views. The drawings illustrate generally, by way of example, but not by way of limitation, various embodiments discussed in the present document.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

This document discusses, among other things, a method and system for optimizing therapies based on mechanical performance of the heart as indicated by heart sounds. Heart sounds, or generally energies resulted from the heart's mechanical vibrations, indicate the heart's mechanical activities, including the openings and closures of the tricuspid, pulmonary, mitral, and aortic valves. Because hemodynamic performance is ultimately determined by the mechanical synchrony of the heart, heart sounds provide a direct measure of efficacy for a therapy intended to restore the heart's ability to contract in synchrony.

Throughout this document, "heart sound" includes audible and inaudible mechanical vibrations caused by cardiac mechanical activities that can be sensed with an accelerometer. S1 generally refers to a heart sound type known as the "first heart sound," or as one or more occurrences or instances of the first heart sound, depending on the context. S2 generally refers to a heart sound type known as the "second heart sound," or as one or more occurrences or instances of the second heart sound, depending on the context. A "user" includes a physician or other caregiver who examines and/or treats a patient using one or more of the methods and apparatuses reported in the present document.

Figure 1:
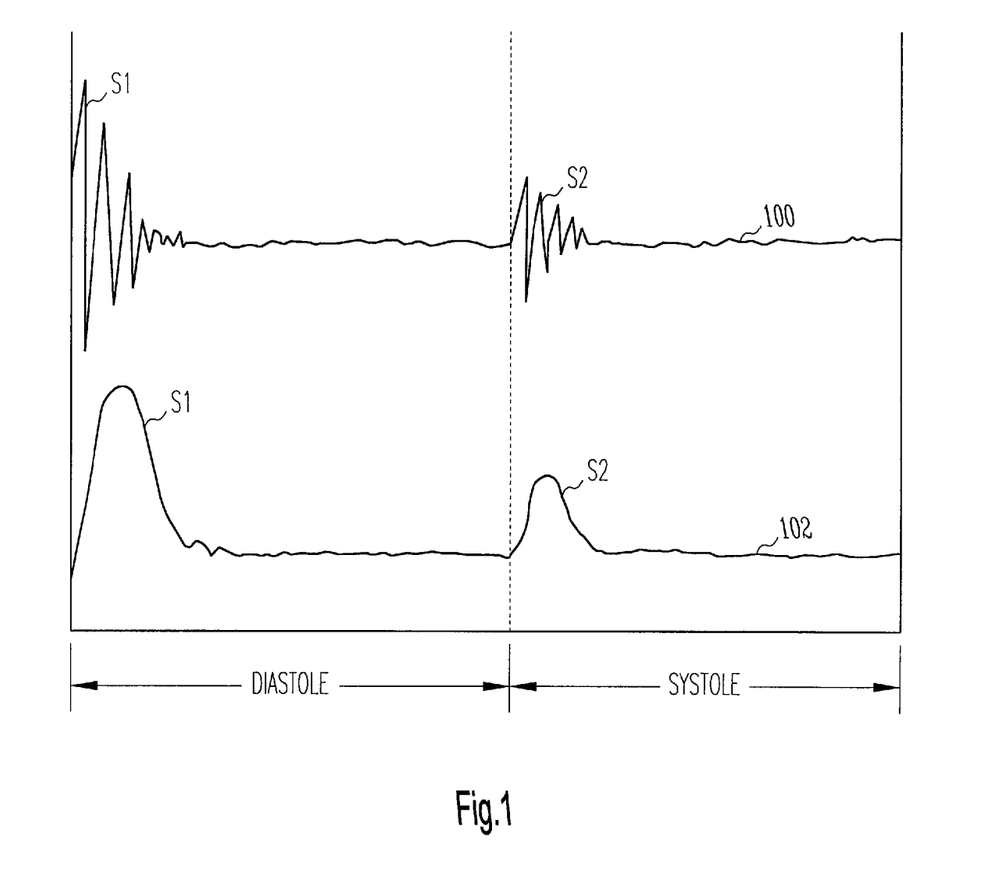
FIG. 1 is a graph illustrating a sensed heart sound signal before and after envelope detection.

FIG. 1 is a graph illustrating a sensed heart sound signal 100 and a processed heart sound signal 102 over one cardiac cycle. Both signals 100 and 102 indicate S1 and S2. Sensed heart sound signal 100 represents an output of a heart sound sensor such as an accelerometer sensing the heart's mechanical vibrations or a microphone sensing audible sound originated from the heart. The signal is conditioned by at least envelope detection to produce heart sound signal 102. In the system and method descriptions below, a "heart sound signal" refers to either a heart sound signal as an output of a heart sound sensor, such as illustrated by signal 100, or a heart sound signal that has been envelope detected, such as illustrated by signal 102.

Each cardiac cycle includes a diastolic phase, during which blood fills the RV through the tricuspid valve and the LV through mitral valve, and a systolic phase, during which the blood are ejected from the RV through the pulmonary valve and the LV through the aortic valve. S1 is known to originate from, among other things, the mechanical vibrations associated with tricuspid valve closure and mitral valve closure, which start the diastolic phase. S2 is known to originate from, among other things, the mechanical vibrations associated with pulmonary valve closure and aortic valve closure, which start the systolic phase.

Figure 2:
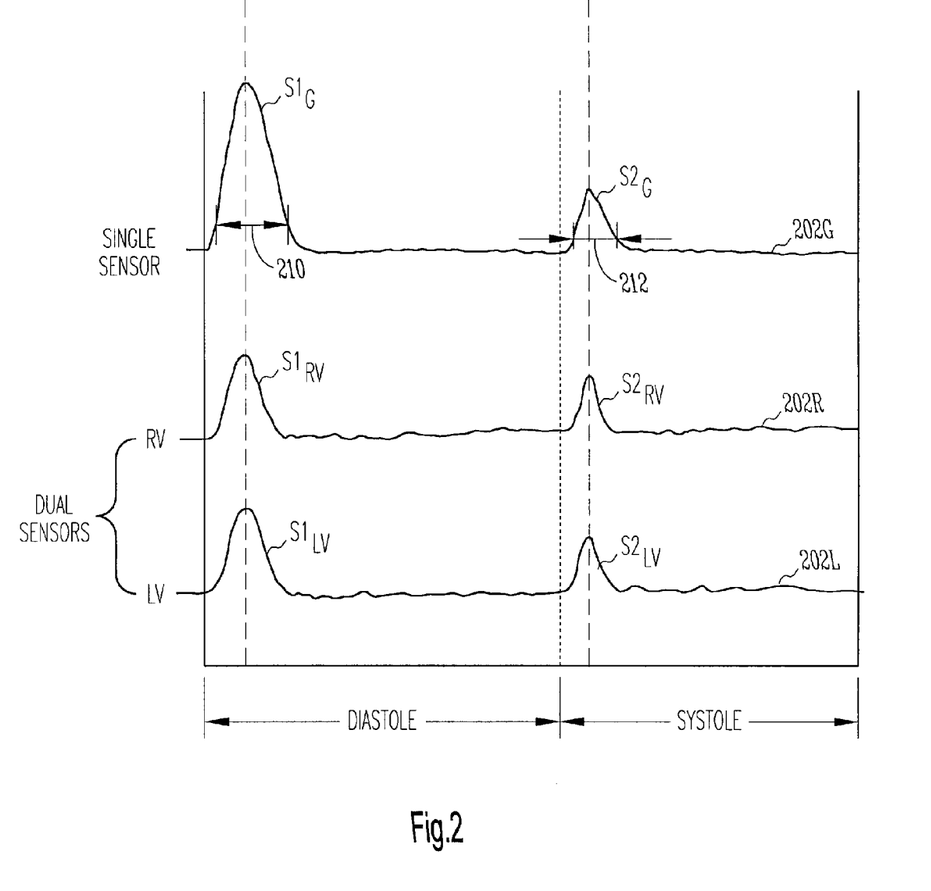
FIG. 2 is a graph illustrating heart sound signals indicative of cardiac mechanical synchrony sensed by various heart sound sensors.

FIG. 2 is a graph illustrating heart sound signals indicative of cardiac mechanical synchrony sensed by various heart sound sensors over a cardiac cycle. A "global" heart sound signal 202G is sensed by a single heart sound sensor sensing heart sounds originated from the entire heart. Heart sound signal 202G indicates $S1_G$ (global S1) and $S2_G$ (global S2) for heart that contracts synchronously. $S1_G$ is morphologically characterized by a single peak and an S1 width 210 that falls within the normal S1 width range. $S2_G$ is morphologically characterized by a single peak and an S2 width 212 that falls within the normal S2 width range.

"Regional" heart sound signals 202R and 202L are sensed simultaneously using two sensors each primarily sensing heart sounds originated from one portion of the heart, such as the right portion or the left portion. In one embodiment, heart sound signal 202R is sensed by a heart sound sensor placed within the RV, and heart sound signal 202L is sensed by a heart sound sensor placed within the LV. RV heart sound signal 202R indicates $S1_{RV}$ (S1 sensed in the RV) and $S2_{RV}$ (S2 sensed in the RV). $S1_{RV}$ indicates tricuspid valve closure. $S2_{RV}$ indicates pulmonary valve closure. LV heart sound signal 202L indicates $S1_{LV}$ (S1 sensed in the LV) and $S2_{LV}$ (S2 sensed in the LV). $S1_{LV}$ indicates mitral valve closure. $S2_{LV}$ indicates aortic valve closure.

In a heart that contracts in synchrony, tricuspid valve closure ($S1_{RV}$) and mitral valve closure ($S1_{LV}$) occur substantially simultaneously. The sounds of tricuspid valve closure and mitral valve closure substantially overlap, producing the normal $S1_G$. Pulmonary valve closure ($S2_{LV}$) and aortic valve closure ($S2_{RV}$) occur substantially simultaneously. The sounds of pulmonary valve closure and aortic valve closure substantially overlap, producing the normal $S2_G$.

Figure 3:
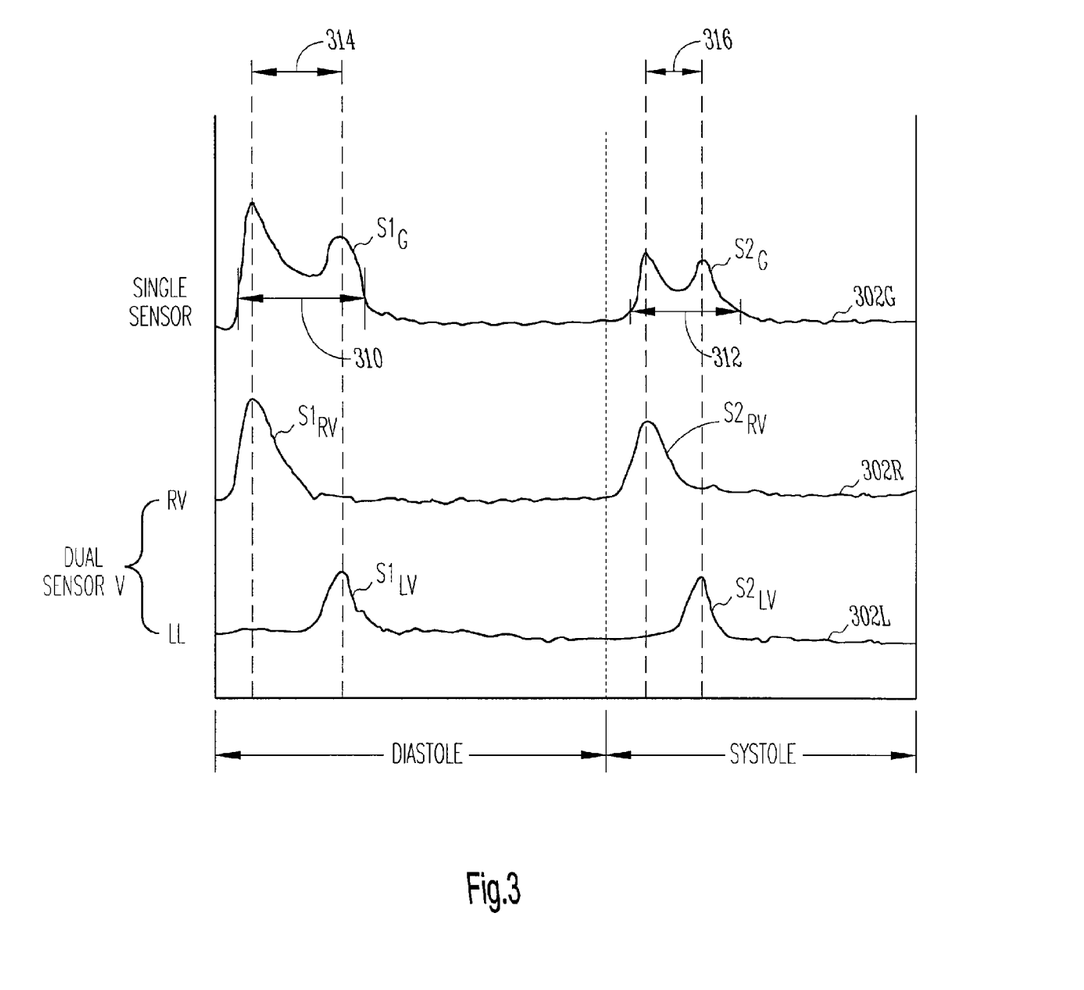
FIG. 3 is a graph illustrating heart sound signals indicative of cardiac mechanical dyssynchrony sensed by various heart sound sensors.

FIG. 3 is a graph illustrating heart sound signals indicative of cardiac mechanical dyssynchrony sensed by various heart sound sensors over a cardiac cycle. A "global" heard sound signal 302G is sensed by a single heart sound sensor sensing heart sounds originated from the entire heart. "Regional" heart sound signals 302R and 302L are sensed simultaneously using two sensors each primarily sensing heart sounds originated from one portion of the heart. Heart sound signal 302G corresponds to heart sound signal 202G, heart sound signal 302R corresponds to heart sound signal 202R, and heart sound signal 302L corresponds to heart sound signal 202L. While signals 202G, 202R, and 202L illustrates heart sound signals indicative cardiac synchrony, signals 302G, 302R, and 302L illustrates heart sound signals indicative cardiac dyssynchrony.

When the cardiac muscles in various regions of the heart fail to contract in synchrony, i.e., when cardiac mechanical dyssynchrony occurs, relative timing between the valve closures deviates from their normal timing. A delay 314 between tricuspid valve closure ($S1_{RV}$) and mitral valve closure ($S1_{LV}$) indicates that the tricuspid valve and the mitral valve no longer close substantially simultaneously. The delay results in a double peaked $S1_G$, and/or an abnormally large S1 width 310 associated with $S1_G$. A delay 316 between pulmonary valve closure ($S2_{RV}$) and aortic valve closure ($S2_{LV}$) indicates that the pulmonary valve and the aortic valve no longer close substantially simultaneously. The delay results in a double peaked $S2_G$, and/or an abnormally large S2 width 312 associated with $S2_G$. Depends on individual conditions, a heart that fails to contract in synchrony may be indicated by one or more of delay 314 and delay 316 and/or one or more of S1 width 310 and S2 width 312.

It is to be understood that the relative timing between $S1_{RV}$ and $S1_{LV}$ and the relative timing between $S2_{RV}$ and $S2_{LV}$ as shown in FIG. 3 represents an example for illustrative purpose only. FIG. 3 shows exemplary heart sound signals of a patient suffering left bundle branch block (LBBB), in which $S1_{RV}$ leads $S1_{LV}$ in time, and $S2_{RV}$ leads $S2_{LV}$ in time. However, the system and method discussed below are generally applicable to cardiac mechanical dyssynchrony indicated by any one or more of delay 314, delay 316, an abnormally long S1 width 310, and an abnormally long S2 width 312.

An effective treatment to resynchronize the heart shortens or eliminates either or both delays 314 and 316 and restores both widths 310 and 312 to their normal values. In other words, the goals of the treatment include (i) merging the two peaks of $S1_G$, and merging the two peaks of $S2_G$, or (ii) realigning $S1_{RV}$ and $S1_{LV}$, and realigning $S2_{RV}$ and $S2_{LV}$. In case the goal with respect to S1 and the goal with respect to S2 cannot be both met, higher priority is given to the goal of (i) merging the two peaks of $S2_G$, or (ii) realigning $S2_{RV}$ and $S2_{LV}$.

One example of such treatment is the application of cardiac resynchronization therapy (CRT), which resynchronizes the contractions of the heart, particularly the ventricles, by delivering ventricular pacing pulses using proper timing. The extent to which a therapy restores cardiac synchrony is indicated by the extent to which delay 314 or 316 are reduced, or by the extent to which width 310 and 312 returned to their normal values.

In system and method descriptions below, heart sound signals 302G, 302R, and 302L, and heart sounds $S1_G$, $S2_G$, $S1_{RV}$, $S2_{RV}$, $S1_{LV}$, and $S2_{LV}$ are used for illustrative, but not restrictive, purposes. Heart sound signal 302G generally includes a "global" heart sound sensed by a single sensor and indicative of heart sounds originating from anywhere in the heart. Heart sound signals 302R and 302L include two heart sound signals simultaneously by two sensors. Heart sound signal 302R generally includes a "regional" heart sound indicative of primarily heart sounds originating from the right side of the heart, sensed by such as a sensor placed in the RV. Heart sound signal 302L generally includes another "regional" heart sound indicative of primarily heart sounds originating from the left side of the heart, sensed by such as a sensor placed in the LV. $S1_G$ generally includes a heart sound resulted from a combination of tricuspid valve closure and mitral valve closure. $S2_G$ generally includes a heart sound resulted from a combination of pulmonary valve closure and aortic valve closure. $S1_{RV}$ generally includes a heart sound resulted from tricuspid valve closure. $S2_{RV}$ generally includes a heart sound resulted from pulmonary valve closure. $S1_{LV}$ generally includes a heart sound resulted from mitral valve closure. $S2_{LV}$ generally includes a heart sound resulted from aortic valve closure. S1 generally refers to the heart sound type known as the "first heart sound," or as one or more occurrences of the "first heart sounds," including $S1_G$, $S1_{RV}$, and $Sl_{LV}$. S2 generally refers to a heart sound type known as the "second heart sound," or as one or more occurrences of the "second heart sounds," including $S2_G$, $S2_{RV}$, and $S2_{LV}$.

Figure 4:
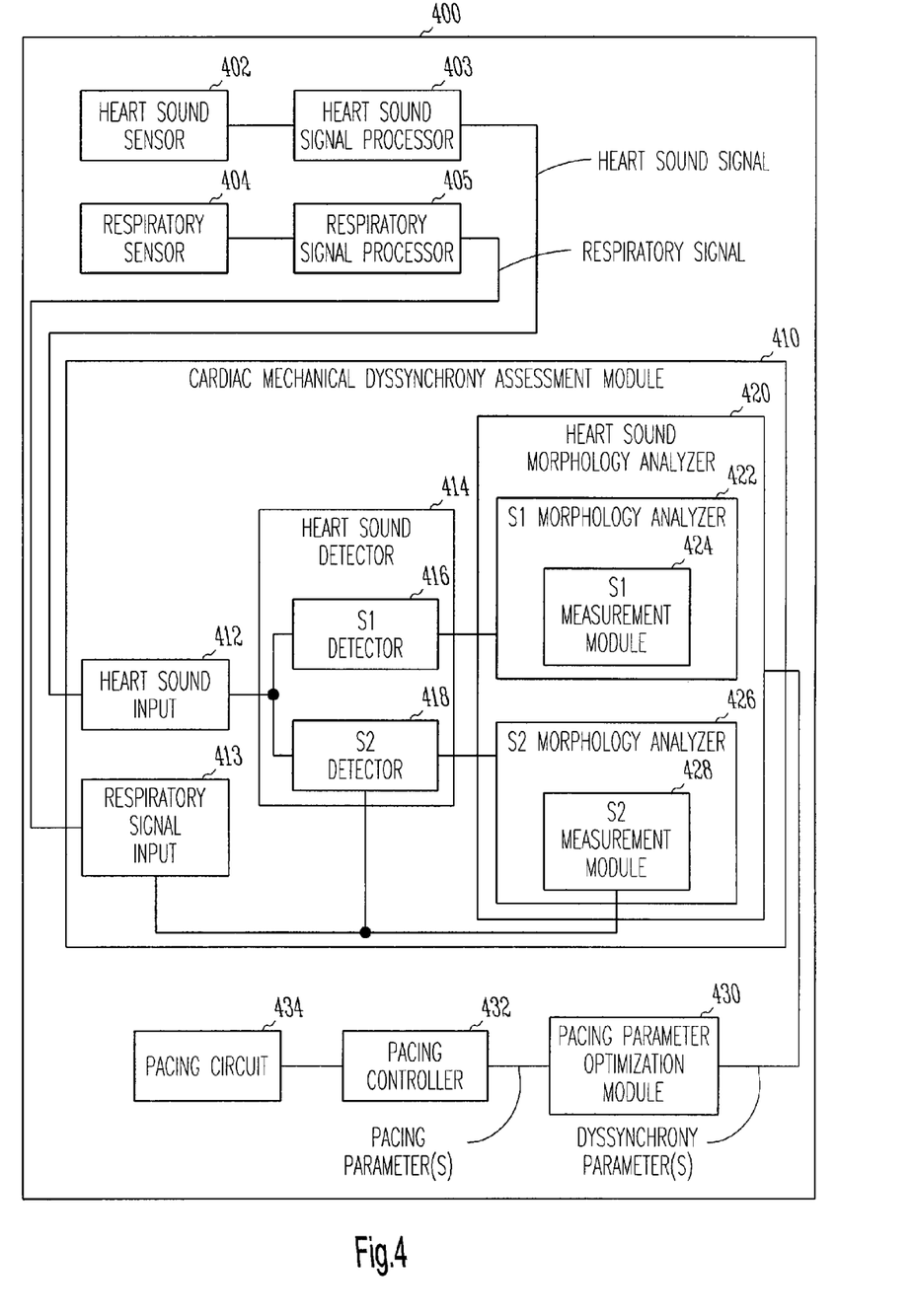
FIG. 4 is a block diagram illustrating one embodiment of a system for optimizing pacing parameters based on a cardiac mechanical dyssynchrony assessment.

FIG. 4 is a block diagram illustrating one embodiment of a system 400 for optimizing pacing parameters based on a cardiac mechanical dyssynchrony assessment. System 400 includes a heart sound sensor 402, a heart sound signal processor 403, a respiratory sensor 404, a respiratory signal processor 405, a cardiac mechanical dyssynchrony assessment module 410, a pacing parameter optimization module 430, a pacing controller 432, and a pacing circuit 434. In one embodiment, portions of system 400 are implemented as a computer-based system.

Heart sound sensor 402 includes one or more sensors each sense a signal indicative of heart sounds. Examples of the one or more sensors include accelerometers and microphones. In one embodiment, heart sound sensor 402 includes a single heart sound sensor to sense a heart sound signal 302G. In one specific embodiment, the single heart sound sensor is placed external to the heart. In another specific embodiment, the single heart sound sensor is placed within a heart chamber. In another embodiment, heart sound sensor 402 is a sensor system including a plurality of heart sound sensors each sensing a signal indicative of heart sounds originating from a particular portion of the heart. In one specific embodiment, the plurality of heart sound sensors include an RV heart sound sensor to sense heart sound signal 302R and an LV heart sound sensor to sense heart sound signal 302L. In one specific embodiment, the RV heart sound sensor is an intracardiac heart sound sensor for placement in the RV to sense a heart sound signal indicative of at least tricuspid valve closure and pulmonary valve closure, and the LV heart sound sensor is another intracardiac heart sound sensor for placement in the LV to sense a heart sound signal indicative of at least mitral valve closure and aortic valve closure. In another specific embodiment, the RV heart sound sensor is the intracardiac heart sound sensor for placement in the RV to sense the heart sound signal indicative of at least tricuspid valve closure and pulmonary valve closure, and the LV heart sound sensor is an epicardial heart sound sensor for placement on the epicardial wall over the LV to sense a heart sound signal indicative of at least mitral valve closure and aortic valve closure.

Heart sound signal processor 403 conditions the one or more heart sound signals sensed by heart sound sensor 402. Heart sound signal processor 403 includes an envelope detector to produce heart sound signal 302G and/or heart sound signals 302R and 302L. In one embodiment, heart sound signal processor 403 further includes an ensemble averaging circuit to improve a signal-to-noise ratio of each of the one or more heart sound signals by ensemble averaging.

Respiratory sensor 404 senses a respiratory signal indicative of respiratory cycles each including an inspiratory phase and expiratory phase. In one embodiment, respiratory sensor 404 includes an accelerometer sensing an acceleration signal indicative of inspiration and expiration. In another embodiment, respiratory sensor 404 includes a minute ventilation sensor. In one specific embodiment, the minute ventilation sensor is an implantable impedance sensor sensing a thoracic impedance indicative of minute ventilation.

Respiration signal processor 405 conditions the respiratory signal for use by cardiac mechanical dyssynchrony assessment module 410. In one embodiment, respiration signal processor 405 includes an expiration detector to detect and indicate each expiratory phase of the respiratory cycle.

Cardiac mechanical dyssynchrony assessment module 410 produces one or more dyssynchrony parameters each indicative of a degree of cardiac mechanical dyssynchrony based on at least the one or more heart sound signals sensed by heart sound sensor 402 and preprocessed by heart sound signal processor 403. Cardiac mechanical dyssynchrony assessment module 410 includes a heart sound input 412, a respiratory signal input 413, a heart sound detector 414, and a heart sound morphology analyzer 420. In one embodiment, cardiac mechanical dyssynchrony assessment module 410 is implemented as a computer-based system. In one specific embodiment, cardiac mechanical dyssynchrony assessment module 410 produces the one or more dyssynchrony parameters by executing an automated cardiac mechanical dyssynchrony algorithm using at least the one or more heard sound signals and/or detected S1 and S2 as input.

Heart sound input 412 receives the one or more heart sound signals, such as heart sound signal 302G and/or heart sound signals 302R and 302L. Respiratory signal input 413 receive the respiratory signal indicative of which occurrences of $S2_G$ and/or $S2_{RV}$ and $S2_{LV}$ are detected during an expiratory phase.

Heart sound detector 414 detects heart sounds from the one or more heart sound signals. Heart sound detector 414 includes at least an S1 detector 416 and an S2 detector 418. In one embodiment, S1 detector 416 detects $S1_G$, and S2 detector 418 detects $S2_G$, both from heart sound signal 302G. In another embodiment, S1 detector 416 detects $S1_{RV}$ from heart sound signal 302R and $S1_{LV}$ from heart sound signal 302L, and S2 detector 418 detects $S2_{RV}$ from heart sound signal 302R and $S2_{LV}$ from heart sound signal 302L.

Heart sound morphology analyzer 420 produces one or more dyssynchrony parameters. In one embodiment, heart sound morphology analyzer 420 is a computer-based analyzer that produces the one or more dyssynchrony parameters by executing the automated cardiac mechanical dyssynchrony algorithm. The automated cardiac mechanical dyssynchrony algorithm is designed to detect morphological features of detected S1 and S2, make measurements related to the morphological features, and produce the one or more dyssynchrony parameters based on results of the measurements, as described below.

Heart sound morphology analyzer 420 includes at least an S1 morphology analyzer 422 to produce a dyssynchrony parameter related to $S1_G$ (or $S1_{RV}$ and $S1_{LV}$) and an S2 morphology analyzer 426 to produce another dyssynchrony parameter related to $S2_G$ (or $S2_{RV}$ and $S2_{LV}$). In one embodiment, S2 morphology analyzer 426 to produce the dyssynchrony parameter related to $S2_G$ (or $S2_{RV}$ and $S2_{LV}$) based on only on $S2_G$ (or $S2_{RV}$ and $S2_{LV}$) detected during an expiratory phase of the respiratory cycle. Heart sound morphology analyzer 420 includes one or more heart sound measurement modules to measure parameters associated with the morphological features of the one or more heart sounds. S1 morphology analyzer 422 includes an S1 measurement module 424. S2 morphology analyzer 426 includes an S2 width measurement module 428.

In one embodiment, each heart sound measurement module includes a heart sound width measurement module to measure widths of the heart sounds. S1 measurement module 424 includes an S1 width measurement module to measure S1 width 310 (the width of $S1_G$). S2 measurement module 428 includes an S2 width measurement module to measure S2 width 312 (the width of $S2_G$).

In another embodiment, each heart sound measurement module includes a heart sound delay measurement modules to measure delays in cardiac valve closure as indicated by heart sounds in a single heart sound signal such as heart sound signal 302G. Each heart sound delay measurement module includes a peak detector and a timer. The peak detector detects peaks within a heart sound each indicating one valve closure. If two peaks are detected within the heart sound, the timer measures the delay as the time interval between the two peaks. In this embodiment, S1 measurement module 424 includes an S1 delay measurement measure to measure S1 delay 314 as a time interval between two peaks detected within $S1_G$. S2 measurement module 428 includes an S2 delay measurement measure to measure S2 delay 316 as a time interval between two peaks detected within $S2_G$. In one embodiment, an imaging technique, such as tissue Doppler imaging (TDI), echocardiography, or magnetic resonance imaging (MRI), is applied to differentiate between the two peaks of $S1_G$. This provides for identification of the peak associated with tricuspid valve closure and the peak associated with mitral valve closure in $S1_G$. Normally, the pulmonary valve closure is delayed during an inspiratory phase. In one embodiment, this fact is utilized to differentiate between the two peaks of $S2_G$. This provides for identification of the peak associated with pulmonary valve closure and the peak associated with aortic valve closure in $S2_G$. In one embodiment, each heart sound measurement modules of morphology analyzer 420 is calibrated on a periodic basis or as needed using these peak identification techniques.

In another embodiment, each heart sound measurement module includes a heart sound delay measurement modules to measure delays in cardiac valve closure as indicated by heart sounds in two heart sound signals such as heart sound signals 302R and 302L. Each heart sound delay measurement module includes a timer to measure the delay being a time interval between a heart sound detected in one heart sound signal and the heart sound detected in another heart sound signal. In this embodiment, S1 measurement module 424 includes an S1 delay measurement module to measure S1 delay 314 as the time interval between $S1_{RV}$ and $S1_{LV}$. S2 measurement module 428 includes an S2 delay measurement module to measure S2 delay 316 as the time interval between $S2_{RV}$ and $S2_{LV}$.

In another embodiment, heart sound morphology analyzer 420 includes a heart sound time-frequency analyzer to produce at least one time-frequency representation for each of the one or more heart sound signals and produce the one or more dyssynchrony parameters each associated with at least one feature of the one time-frequency representation. In one embodiment, the heart sound time-frequency analyzer further produces a parameter indicative of pulmonary artery pressure based on at least one feature of the time-frequency representation. The heart sound time-frequency analyzer includes, by way of example, and not by way of limitation, one or more of a short-time Fourier transform (STFT) module, a reduced interference (RID) module, and a wavelet transform (WT) module. The STFT module produces a time versus frequency representation of the signal by applying a sliding window to data representing the one or more heart sound signals. A spectral representation based on a windowed Fourier transform (FT) is computed each time the window position is updated. The RID module provides an improvement in resolution over the STFT based on the Wigner-Ville time-frequency distribution by presenting a result with reduced interference. The WT module takes advantage of the fact that higher frequencies are better resolved in time while lower frequencies are better resolved in frequency. This processing involves recursively filtering the data representing the one or more heart sound signals at different scales with sets of high-pass and low-pass filters.

Pacing parameter optimization module 430 determines one or more approximately optimal pacing parameters based on the one or more dyssynchrony parameters. The approximately optimal pacing parameters provide for an approximately minimum degree of cardiac mechanical dyssynchrony. Pacing controller 432 controls the delivery of pacing pulses to the heart from pacing circuit 434 using parameters provided by pacing parameter optimization module 430 for evaluating the parameters by their effects on the degree of cardiac mechanical dyssynchrony. The approximately optimal pacing parameters are determined by selecting parameters associated with the lowest degree of degree of cardiac mechanical dyssynchrony, as indicated by the one or more dyssynchrony parameters, from all the parameters evaluated.

In one embodiment, pacing parameter optimization module 430 optimizes one or more pacing parameters by adjusting the one or more pacing parameters for an approximately optimal value of each of the one or more dyssynchrony parameters. The approximately optimal value is a value associated with the minimum degree of cardiac mechanical dyssynchrony obtained by the adjusting the one or more pacing parameters. Pacing parameter optimization module 430 includes a parameter adjustment circuit to adjust the one or more pacing parameters. The parameter adjustment circuit includes, but is not limited to, one or more of a pacing site selector, an atrioventricular delay (AVD) adjustment circuit, and an interventricular delay (IVD) adjustment circuit. The pacing site selector selects one or more pacing sites to which the pacing pulses are delivered. The AVD adjustment circuit adjusts one or more AVDs at which ventricular pacing pulses are delivered. The IVD adjustment circuit adjusts one or more IVDs at which ventricular pacing pulses are delivered. After each adjustment of any one or more of the pacing sites, AVDs, and IVDs, pacing controller 432 controls the delivery of the pacing pulses from pacing circuit 434 using the adjusted parameters. The optimization process includes repeated parameter adjustments and deliveries of pacing pulses using the adjusted parameters until an approximately minimum or otherwise satisfactory degree of cardiac mechanical dyssynchrony is reached.

In another embodiment, pacing parameter optimization module 430 optimizes one or more pacing parameters by testing various combinations of values for the one or more pacing parameters for their effects on the degree of cardiac mechanical dyssynchrony. Pacing parameter optimization module 430 includes a parameter generator to generate a plurality of pacing parameter value sets each including a value for each of the one or more pacing parameters. The parameter generator includes, but is not limited to, one or more of a pacing site generator, an AVD generator, and an IVD generator. The pacing site generator generates a plurality of pacing sites or pacing site combinations to which the pacing pulses are delivered. The AVD generator generates a plurality of AVDs at which ventricular pacing pulses are delivered. The IVD generator generates a plurality of IVDs at which ventricular pacing pulses are delivered. In one embodiment where more than one pacing parameter is being tested, each of the pacing parameter value sets includes a unique combination of values for the tested parameters. Pacing controller 432 controls the delivery of a plurality of pacing pulse sequences from pacing circuit 434. Each sequence includes a plurality of pacing pulses delivered using one of the pacing parameter value sets. The optimization process includes identifying the pacing parameter value set that produces an approximately minimum or otherwise satisfactory degree of cardiac mechanical dyssynchrony. In one embodiment, pacing parameter optimization module 430 includes an optimal parameter selector to select an optimal parameter value set associated with the minimum degree of cardiac mechanical dyssynchrony produced by pacing during the optimization process.

It is to be understood that while optimization of pacing parameters, and particularly the pacing sites, AVDs, and IVDs are discussed as examples, the idea of adjusting or optimizing a therapy using a measure of cardiac mechanical dyssynchrony is not limited to the optimization of pacing therapy. The basic concept of adjusting or optimizing a therapy by determining therapy parameters providing for a minimum degree of cardiac mechanical dyssynchrony generally applies to the optimization of other pacing parameters and other therapies including, but not being limited to, other electrical therapies, physical therapies, chemical therapies, and biological therapies.

Figure 5:
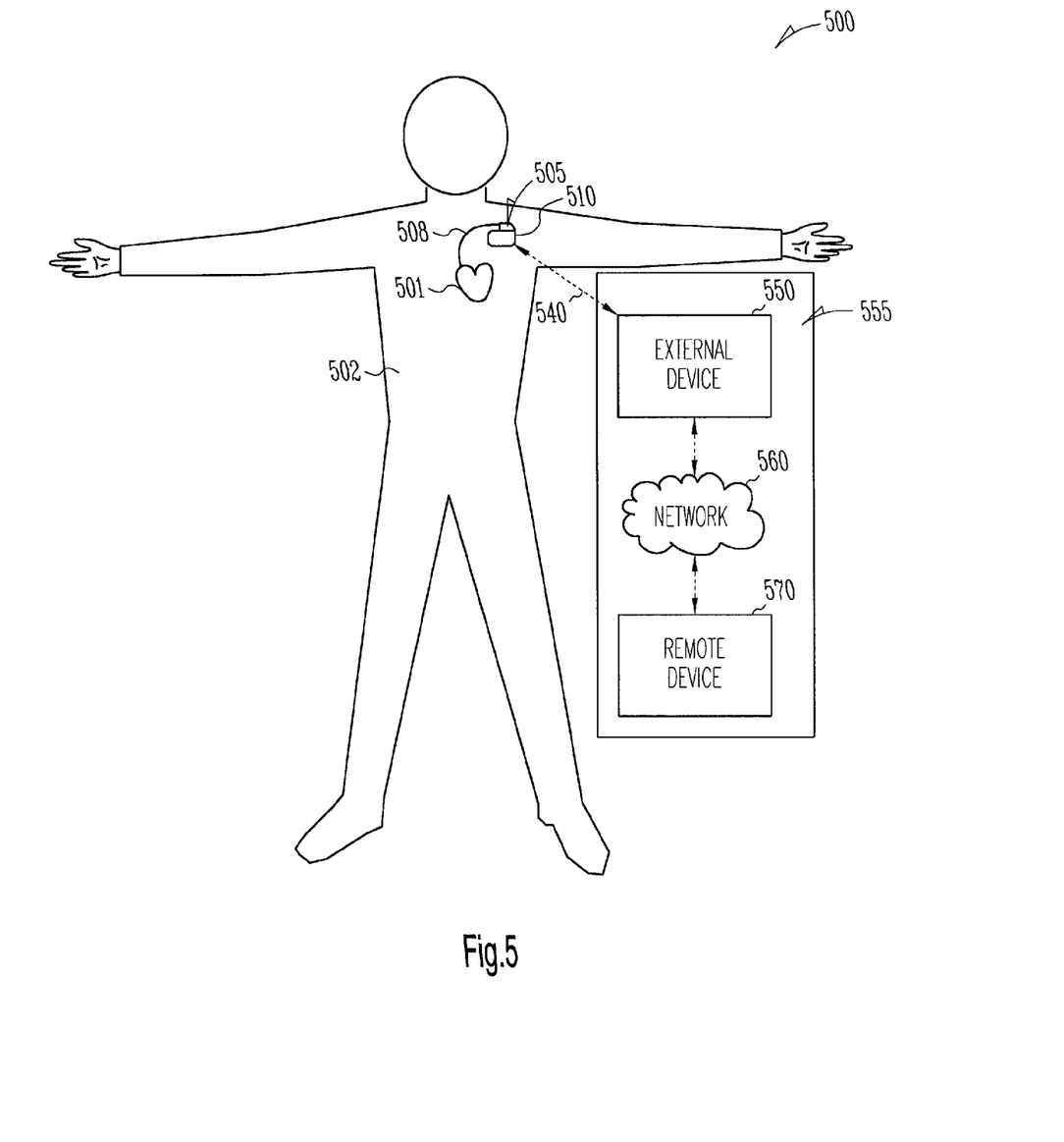
FIG. 5 is an illustration of one embodiment of a CRM system and portions of the environment in which the CRM system is used.

FIG. 5 is an illustration of one embodiment of a cardiac rhythm management (CRM) system 500 and portions of the environment in which system 500 is used. System 500 includes an implantable system 505, an external system 555, and a telemetry link 540 providing for communication between implantable system 505 and external system 555.

Implantable system 505 includes, among other things, implantable medical device 510 and lead system 508. In various embodiments, implantable medical device 510 is an implantable CRM device including one or more of a pacemaker, a cardioverter/defibrillator, a cardiac resynchronization therapy (CRT) device, a cardiac remodeling control therapy (RCT) device, a drug delivery device, and a biological therapy device. In one embodiment, implantable medical device 510 includes implantable sensors for sensing the signals used by cardiac mechanical dyssynchrony assessment module 410 and pacing parameter optimization module 430. In another embodiment, implantable medical device 510 and lead system 508 each include one or more of the implantable sensors. As shown in FIG. 5, implantable medical device 510 is implanted in a body 502. Lead system 508 provides connections between implantable medical device 510 and a heart 501. In various embodiments, lead system 508 includes leads for sensing physiological signals and delivering pacing pulses, cardioversion/defibrillation shocks, and/or pharmaceutical or other substances. In one embodiment, at least one implantable sensor is incorporated into a lead of lead system 508 for placement in or about heart 501.

In one embodiment, external system 555 is a patient management system including external device 550, network 560, and remote device 570. External device 550 is within the vicinity of implantable medical device 510 and communicates with implantable medical device 510 bi-directionally via telemetry link 540. Remote device 570 is in a remote location and communicates with external device 550 bi-directionally via network 560, thus allowing a user to monitor and treat a patient from a distant location. In another embodiment, external system includes a programmer communicating with implantable medical device 510 bi-directionally via telemetry link 540.

System 500 includes system 400 for optimizing pacing parameters based on the cardiac mechanical dyssynchrony assessment. In one embodiment, system 500 also serves diagnostic and/or other therapeutic purposes by providing the user with heart sound signals indicative of cardiac mechanical dyssynchrony and/or other cardiovascular conditions. The distribution of system 400 in system 500 depends on design and patient management considerations, such as the size and power consumption of each system component and the ability of monitoring the patient in various settings from various locations. In one embodiment, implantable medical device 510 includes the entire system 400. In another embodiment, implantable medical device 510 includes portions of system 400, and external system 555 includes the remaining portions of system 400. One specific embodiment is discussed below with reference to FIG. 6 as an example, but not a limitation.

Figure 6:
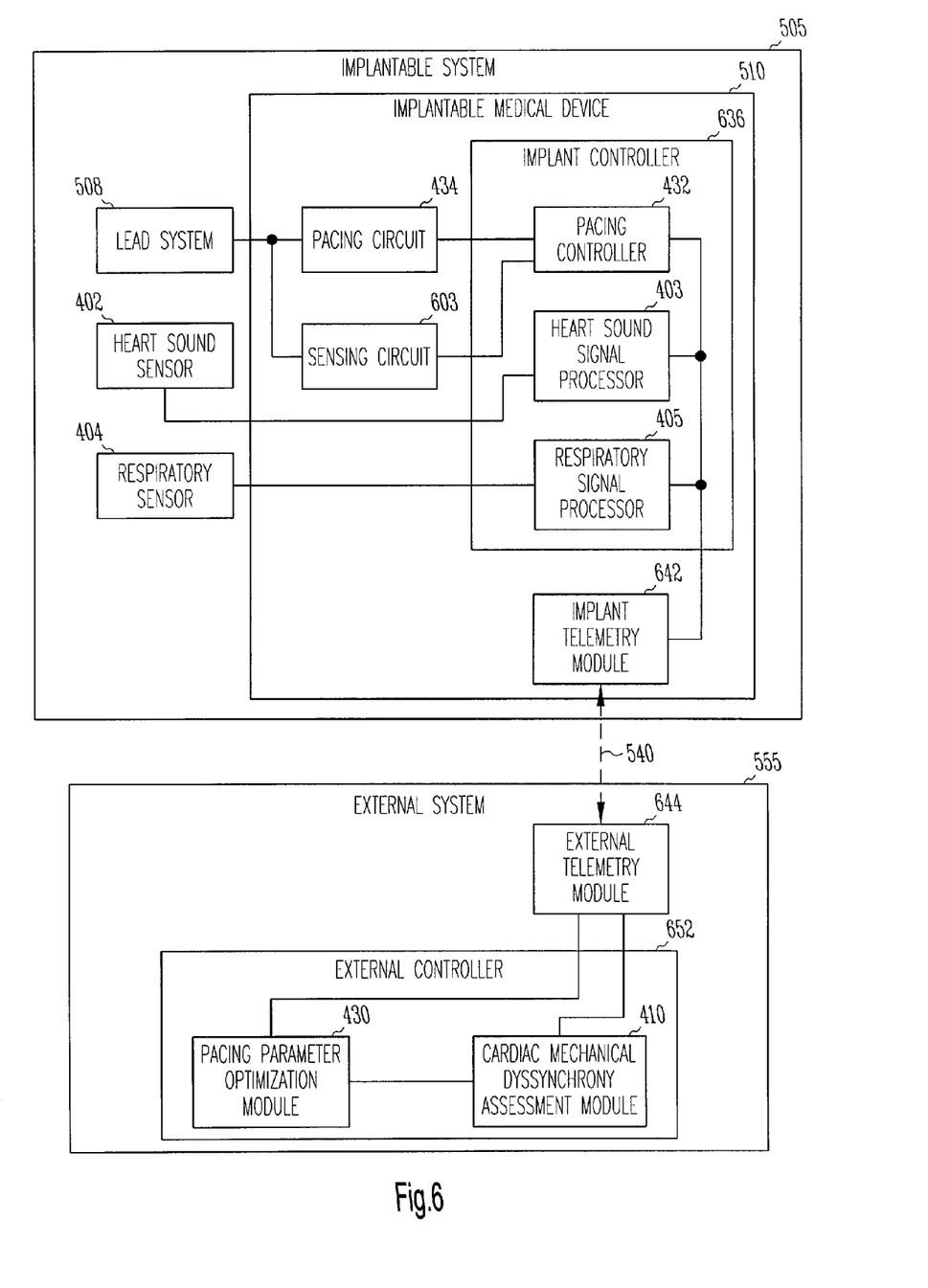
FIG. 6 is a block diagram illustrating one embodiment of a circuit of the CRM system.

FIG. 6 is a block diagram illustrating one embodiment of a circuit of system 500, including implantable system 505, external system 555, and telemetry link 540 wirelessly coupling the two systems.

Implantable system 505 includes lead system 508, heart sound sensor 402, respiratory sensor 404, and implantable medical device 510. Lead system 508 includes pacing leads each having at least one electrode to be placed in a heart chamber. Each pacing lead allows delivery of pacing pulses to, and sensing of cardiac electrical activity from, a cardiac location where the electrode is placed. In one embodiment, lead system 508 includes one or more atrial pacing leads and one or more ventricular pacing leads. The one or more atrial pacing leads include at least one RA pacing lead. The one or more ventricular pacing leads include one or more RV pacing lead and/or one or more LV pacing leads. In one embodiment, heart sound sensor 402 includes one sensor housed in implantable medical device 510 to sense heart sound signal 302G. In another embodiment, heart sound sensor 402 includes one intracardiac sensor incorporated into a pacing lead of lead system 508 for placement within a heart chamber to sense heart sound signal 302G. In another embodiment, heart sound sensor 402 includes one intracardiac sensor incorporated into an RV pacing lead to sense heart sound signal 302R and another intracardiac sensor or epicardial sensor incorporated into an LV pacing lead to sense heart sound signal 302L. In one embodiment, respiratory sensor 404 is housed in implantable medical device 510. In another embodiment, respiratory sensor 404 is incorporated into a pacing lead of lead system 508 for placement within a heart chamber. Implantable medical device 510 includes pacing circuit 434, a sensing circuit 603, an implant controller 636, and an implant telemetry module 642. Pacing circuit 434 produces pacing pulses and delivers the pacing pulses to the heart through lead system 508. Sensing circuit 603 senses electrograms indicative of cardiac electrical activities. Implant controller 636 includes at least pacing controller 432, heart sound signal processor 403, and respiratory signal processor 405. Pacing controller 432 controls pacing circuit 434 by executing a selected pacing algorithm using at least the cardiac activities sensed by sensing circuit 603 and pacing parameters programmed into implant controller 636 as inputs.

External system 555 includes an external telemetry module 644 and an external controller 652. External controller 652 includes cardiac mechanical dyssynchrony assessment module 410 and pacing parameter optimization module 430. In one embodiment, in which external system 555 includes external device 550, network 560, and remote device 570, remote device 570 includes cardiac mechanical dyssynchrony assessment module 410 and pacing parameter optimization module 430. This allows long-term therapy optimization performed by the user, or by system 500 automatically, in a location away from the patient's presence. In one embodiment, system 500 provides for therapy optimization on a continuous basis. In another embodiment, system 500 provides for therapy optimization on a predetermined schedule, such as on a periodic basis. In another embodiment, system 500 provides for therapy optimization in response to a change of patient condition detected by or through implantable system 505. In another embodiment, system 500 provides for therapy optimization in response to a command entered by the user. The therapy optimization results in one or more optimal pacing parameter values to be programmed into implant controller 636.

Implant telemetry module 642 and external telemetry module 644 support telemetry link 540. Telemetry link 540 is a wireless bidirectional data transmission link. In one embodiment, telemetry link 540 is an inductive couple formed when two coils—one connected to implant telemetry module 642 and the other connected to external telemetry module 644—are placed near each other. In this embodiment, the patient or the user places the coil connected to external device 550 on body 502 over implantable medical device 510. In another embodiment, telemetry link 540 is a far-field radio-frequency telemetry link allowing implantable medical device 510 and external device 550 to communicate over a telemetry range that is at least ten feet. In one embodiment, implant telemetry module 642 transmits the heart sound and respiratory signals acquired by implantable system 505, and external telemetry module 644 receives these signals.

Figure 7:
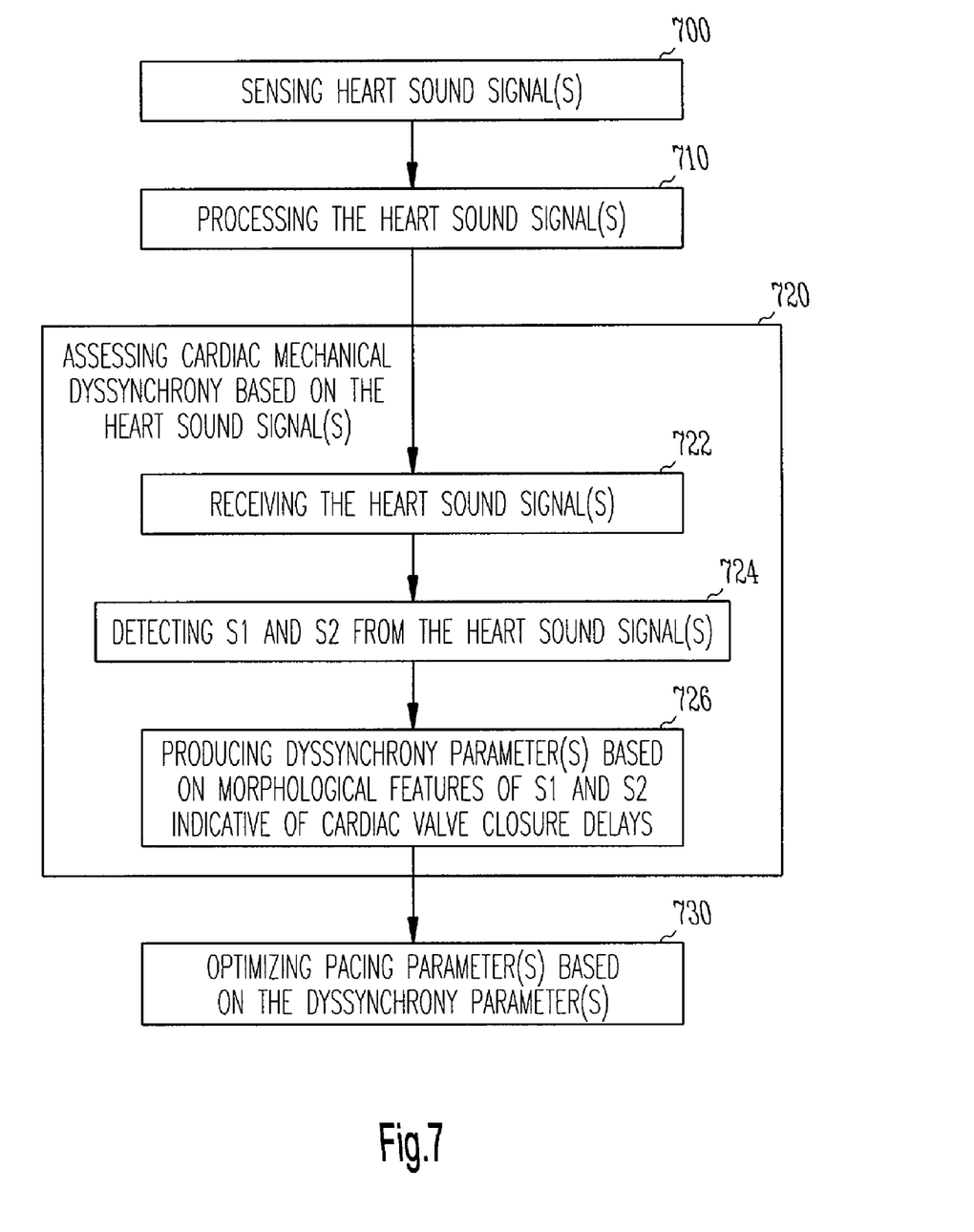
FIG. 7 is a flow chart illustrating one embodiment of a method for optimizing pacing parameters based on the cardiac mechanical dyssynchrony assessment.

FIG. 7 is a flow chart illustrating one embodiment of a method for optimizing pacing parameters based on the cardiac mechanical dyssynchrony assessment. In one embodiment, the method is performed by system 400.

One or more heart sound signals indicative of at least S1 and S2 are sensed at 700. In one embodiment, the one or more heart sound signals include one or more acceleration signals indicative of the heart's mechanical vibrations. In another embodiment, the one or more heart sound signals include one or more audio signals originated from the heart. In one embodiment, heart sound signal 302G is sensed at 700. In another embodiment, heart sound signals 302R and 302L are sensed at 700. In another embodiment, both heart sound signal 302G and heart sound signals 302R and 302L are sensed at 700. In one embodiment, a respiratory signal indicative of respiratory cycles each including an inspiratory phase and expiratory phase is also sensed. In one specific embodiment, the respiratory signal includes an impedance signal indicative minute ventilation.

The one or more heart sound signals are processed at 710. The process includes envelope-detecting the one or more heart sound signals by rectification and low-pass filtering. In one embodiment, each envelope-detected heart sound signal is ensemble averaged to improve its signal-to-noise ratio. In one embodiment, the respiratory signal is also processed at 710. The process includes detection of expiratory phases.

Cardiac mechanical dyssynchrony is assessed based on the one or more heart sound signals at 720. The one or more heart sound signals are received at 722. In one embodiment, the respiratory signal is also received at 722. In one embodiment, only $S2_G$, and/or $S2_{RV}$ and $S2_{LV}$, that occur during the expiratory phase of the respiratory cycle are used for the assessment of cardiac mechanical dyssynchrony. S1 and S2 are detected from the one or more heart sound signals at 724. In one embodiment, $S1_G$ and $S2_G$ are detected from heart sound signal 302G. In another embodiment, $S1_{RV}$ and $S2_{RV}$ are detected from heart sound signal 302R, and $S1_{LV}$ and $S2_{LV}$ are detected from heart sound signal 302L. One or more dyssynchrony parameters each indicative of the degree of cardiac mechanical dyssynchrony are produced based on morphological features of, or related to, S1 and S2 at 726. In one embodiment, an automated cardiac mechanical dyssynchrony algorithm is executed to detect morphological features of detected S1 and S2, make measurements related to the morphological features, and produce the one or more dyssynchrony parameters based on results of the measurements at 726. The morphological features indicate cardiac valve closure delays. In one embodiment, a first dyssynchrony parameter related to S1 and a second dyssynchrony parameter related to S2 are produced at 726. The production of the dyssynchrony parameters includes measuring one or more parameters associated with the morphological features.

In one embodiment, S1 width 310 and S2 width 312 are measured from heart sound signal 302G. In another embodiment, S1 delay 314 and S2 delay 316 are measured from heart sound signal 302G. S1 delay 314 is measured as the time interval between the peak of $S1_G$ associated with mitral valve closure and the peak of $S1_G$ associated with tricuspid valve closure. S2 delay 316 is measured as the time interval between the peak $S2_G$ associated with aortic valve closure and the peak $S2_G$ associated with pulmonary valve closure. In another embodiment, S1 delay 314 and S2 delay 316 are measured from heart sound signals 302R and 302L. S1 delay 314 is measured as the time interval between $S1_{RV}$ and $S1_{LV}$. S2 delay 316 is measured as the time interval between $S2_{RV}$ and $S2_{LV}$. In another embodiment, at least one time-frequency representation for each of the one or more heart sound signals is produced. The time-frequency representation is produced by, for example, performing one or more of STFT, RID, and WT. One or more dyssynchrony parameters are produced each based on at least one feature in the time-frequency representation. In a further embodiment, a parameter is produced to indicate pulmonary artery pressure based on at least one feature in the time-frequency representation.

One or more pacing parameters are optimized at 730, based on the one or more dyssynchrony parameters produced at 726. The one or more parameters are optimized when the one or more dyssynchrony parameters indicate an approximately minimum degree of cardiac mechanical dyssynchrony. In one embodiment, the one or more pacing parameters are optimized based on at least one dyssynchrony parameter produced based on S2 measurements. The optimization is to minimize the time interval between pulmonary valve closure and aortic valve closure. In another embodiment, the one or more pacing parameters are optimized based on at least one dyssynchrony parameter produced based on S1 measurements. The optimization is to minimize the time interval between tricuspid valve closure and mitral valve closure. In another embodiment, the one or more pacing parameters are optimized based on dyssynchrony parameters produced based on both S1 and S2 measurements. If the time interval between pulmonary valve closure and aortic valve closure and the time interval between tricuspid valve closure and mitral valve closure cannot be minimized with the same one or more pacing parameters, the minimization of the time interval between pulmonary valve closure and aortic valve closure has a higher priority.

In one embodiment, the one or more pacing parameters are adjusted for an approximately optimal value of each of the one or more dyssynchrony parameters. The approximately optimal value is a value associated with an approximately minimum degree of cardiac mechanical dyssynchrony obtained by adjusting the one or more pacing parameters. Adjusting the one or more pacing parameters includes, but is not limited to, selecting one or more pacing sites to which the pacing pulses are delivered, adjusting one or more AVDs at which ventricular pacing pulses are delivered, and adjusting one or more IVDs at which ventricular pacing pulses are delivered. After each parameter adjustment, a plurality of pacing pulses is delivered to the heart using the one or more adjusted pacing parameters. The optimization process includes repeated parameter adjustments and delivery of pacing pulses using the adjusted parameters until an approximately minimum or otherwise satisfactory degree of cardiac mechanical dyssynchrony is reached.

In another embodiment, the one or more pacing parameters are optimized by testing the effects of various combinations of values of the one or more pacing parameters on the one or more dyssynchrony parameters. A plurality of pacing parameter value sets is generated. Each pacing parameter value set includes a value for each of the one or more pacing parameters. Generating the plurality of pacing parameter value sets includes, but is not limited to, generating a plurality of pacing sites or pacing site combinations to which pacing pulses are delivered, generating a plurality of AVDs at which ventricular pacing pulses are delivered, and generating a plurality of IVDs at which ventricular pacing pulses are delivered. After the plurality of pacing parameter value sets are delivered, a plurality of pacing pulse sequences are delivered. Each sequence includes a plurality of pacing pulses delivered using one pacing parameter value set of the plurality of pacing parameter value sets. An optimal parameter value set is selected from the plurality of pacing parameter value sets. The optimal pacing parameter value set is associated with an approximately optimal value of at least one of the one or more dyssynchrony parameters. The approximately optimal value is associated with a minimum degree of cardiac mechanical dyssynchrony obtained by pacing with the plurality of pacing parameter sets.

It is to be understood that the above detailed description is intended to be illustrative, and not restrictive. For example, the method for assessing the cardiac mechanical dyssynchrony can be performed by a non-implantable system. The method for optimizing pacing parameters can apply to optimization of parameters of therapies other than cardiac pacing. Other embodiments, including any possible permutation of the system components discussed in this document, will be apparent to those of skill in the art upon reading and understanding the above description. The scope of the invention should, therefore, be determined with reference to the appended claims, along with the full scope of equivalents to which such claims are entitled.

What is claimed is:

1. A system for pacing a heart having cardiac chambers including right and left ventricles and cardiac valves including tricuspid, mitral, pulmonary, and aortic valves, the system comprising:
   a heart sound input to receive one or more signals indicative of heart sounds;
   a heart sound detector coupled to the heart sound input, the heart sound detector adapted to detect predetermined type heart sounds using the received one or more signals, the predetermined type heart sounds having morphological features indicative of one or more time intervals each between closures of a first cardiac valve and a second cardiac valve in a cardiac cycle, the one or more time intervals each indicative of cardiac mechanical dyssynchrony;
   a heart sound morphology analyzer coupled to the heart sound detector, the heart sound morphology analyzer adapted to measure one or more dyssynchrony parameters each from one heart sound of the detected predetermined type heart sounds and indicative of a time interval of the one or more time intervals; and
   a pacing parameter optimization module coupled to the heart sound morphology analyzer, the pacing parameter optimization module adapted to determine one or more approximately optimal pacing parameters using the one or more dyssynchrony parameters, the one or more approximately optimal pacing parameters providing for an approximately minimum degree of cardiac mechanical dyssynchrony as indicated by the one or more dyssynchrony parameters.

2. The system of claim 1, wherein the heart sound detector is adapted to detect first heart sounds (S1), and the heart sound morphology analyzer comprises an S1 measurement module adapted to measure one or more parameters each indicative of a first time interval between a tricuspid valve closure and a mitral valve closure using the detected S1.

3. The system of claim 1, wherein the heart sound detector is adapted to detect second heart sounds (S2), and the heart sound morphology analyzer comprises an S2 measurement module adapted to measure one or more parameters each indicative of a second time interval between a pulmonary valve closure and an aortic valve closure using the detected S2.

4. The system of claim 1, wherein the heart sound detector is adapted to detect first heart sounds (S1) and second heart sounds (S2), and the heart sound morphology analyzer comprises:
   an S1 measurement module adapted to measure one or more parameters each indicative of a first time interval between a tricuspid valve closure and a mitral valve closure using the detected S1; and
   an S2 measurement module adapted to measure one or more parameters each indicative of a second time interval between a pulmonary valve closure and an aortic valve closure using the detected S2.

5. The system of claim 4, wherein the heart sound input is configured to receive a first signal indicative of S1 sensed from the right ventricle ($S1_{R_v}$) and S2 sensed from the right-ventricle ($S2_{R_v}$) and a second signal indicative of at least S1 sensed from the left ventricle ($S1_{LV}$) and S2 sensed from the left ventricle ($S2_{LV}$), the heart sound detector is adapted to detect $S1_{RV}$ and $S2_{RV}$ using the received first signal and detect $S1_{LV}$ and $S2_{LV}$ using the received second signal, the S1 measurement module is adapted to measure an S1 delay being a time interval between $S1_{RV}$ and $S1_{LV}$, and the S2 measurement module is adapted to measure an S2 delay being a time interval between $S2_{RV}$ and $S2_{LV}$.

6. The system of claim 4, wherein the S1 measurement module is adapted to measure an S1 width, and the S2 measurement module is adapted to measure an S2 width.

7. The system of claim 4, wherein the S1 measurement module is adapted to measure an S1 delay being a time interval between a morphological feature indicative of the tricuspid valve closure and a morphological feature indicative of the mitral valve closure, and the S2 measurement module is adapted to measure an S2 delay being a time interval between a morphological feature indicative of the pulmonary valve closure and a morphological feature indicative of the aortic valve closure.

8. The system of claim 1, wherein the parameter optimization module is adapted to optimize one or more of a pacing site, an atrioventricular delay, and an interventricular delay.

9. A method for operating a cardiac pacemaker, the method comprising:
   receiving one or more heart sound signals;
   detecting predetermined type heart sounds having morphological features indicative of one or more time intervals each between closures of a first cardiac valve and a second cardiac valve in a cardiac cycle, the one or more time intervals each indicative of cardiac mechanical dyssynchrony;
   measuring one or more dyssynchrony parameters each from one heart sound of the detected predetermined type heart sounds and indicative of a time interval of the one or more time intervals; and
   determining one or more approximately optimal pacing parameters using the one or more dyssynchrony parameters, the one or more approximately optimal pacing parameters providing for an approximately minimum degree of cardiac mechanical dyssynchrony as indicated by the one or more dyssynchrony parameters.

10. The method of claim 9, comprising sensing one or more heart sound signals indicative of one or more of first heart sounds (S1) and second heart sounds (S2).

11. The method of claim 10, wherein measuring the one or more dyssynchrony parameters indicative of the one or more time intervals comprises measuring one or more of an S1 width and an S2 width.

12. The method of claim 10, wherein measuring the one or more dyssynchrony parameters indicative of the one or more time intervals comprises measuring one or more of an S1 delay and an S2 delay, the S1 delay representative of a time interval between a tricuspid valve closure and a mitral valve closure during a cardiac cycle, the S2 delay representative of a time interval between a pulmonary valve closure and an aortic valve closure during a cardiac cycle.

13. The method of claim 12, comprising sensing a first heart sound signal from a right ventricle (RV) and sensing a second heart sound signal from a left ventricle (LV).

14. The method of claim 13, comprising sensing a first heart sound signal from RV and a second heart sound from LV, the first heart sound signal indicative of S1 sensed from the RV ($S1_{RV}$) and S2 sensed from the RV ($S2_{RV}$), the second heart sound signal indicative of S1 sensed from the LV ($S1_{LV}$) and S2 sensed from the LV ($S2_{LV}$), and wherein measuring the S1 delay comprises measuring the S1 delay being a time interval between $S1_{RV}$ and $S1_{LV}$, and measuring the S2 delay comprises measuring the S2 delay being a time interval between $S2_{RV}$ and $S2_{LV}$.

15. The method of claim 9, wherein determining the one or more pacing parameters comprises selecting one or more pacing sites to which pacing pulses are delivered.

16. The method of claim 9, wherein determining the one or more pacing parameters comprises determining one or more atrioventricular delays at which ventricular pacing pulses are delivered.

17. The method of claim 9, wherein determining the one or more pacing parameters comprises determining one or more interventricular delays at which ventricular pacing pulses are delivered.

18. A cardiac pacing system, comprising:
 means for detecting predetermined type heart sounds from one or more heart sound signals, the predetermined type heart sounds having morphological features indicative of one or more time intervals each between closures of a first cardiac valve and a second cardiac valve, the one or more time intervals each indicative of cardiac mechanical dyssynchrony;
 means for measuring one or more dyssynchrony parameters each from one heart sound of the detected predetermined type sounds and indicative of a time interval of the one or more time intervals; and
 means for determining one or more approximately optimal pacing parameters using the one or more dyssynchrony parameters, the one or more approximately optimal pacing parameters providing for an approximately minimum degree of cardiac mechanical dyssynchrony as indicated by the one or more dyssynchrony parameters.

19. The system of claim 18, comprising implantable means for sensing the one or more heart sound signals.

20. The system of claim 19, further comprising means for producing at least one dyssynchrony parameter indicative of a degree of cardiac mechanical dyssynchrony using the detected heart sounds having morphological features indicative of one or more time intervals each between closures of the first cardiac valve and the second cardiac valve in a cardiac cycle.

* * * * *

UNITED STATES PATENT AND TRADEMARK OFFICE
CERTIFICATE OF CORRECTION

PATENT NO. : 7,953,484 B2
APPLICATION NO. : 11/687812
DATED : May 31, 2011
INVENTOR(S) : Marina V. Brockway et al.

Page 1 of 1

It is certified that error appears in the above-identified patent and that said Letters Patent is hereby corrected as shown below:

In column 6, line 31, delete "$Sl_{LV}$." and insert -- $S1_{LV}$. --, therefor.

In column 15, lines 61-62, in Claim 5, delete "rightventricle" and insert -- right ventricle --, therefor.

Signed and Sealed this
Ninth Day of August, 2011

David J. Kappos
*Director of the United States Patent and Trademark Office*